United States Patent
Chibane et al.

(10) Patent No.: US 9,310,419 B2
(45) Date of Patent: Apr. 12, 2016

(54) METHOD FOR DETECTING DEFECTIVE ELECTRODES IN A MICRO-ELECTRODE MATRIX

(71) Applicant: COMMISSARIAT A L'ENERGIE ATOMIQUE, Paris (FR)

(72) Inventors: Alexandre Chibane, Grenoble (FR); Pierre Grangeat, Saint Ismier (FR)

(73) Assignee: COMMISSARIAT A L'ENERGIE ATOMIQUE, Paris (FR)

(*) Notice: Subject to any disclaimer, the term of this patent is extended or adjusted under 35 U.S.C. 154(b) by 354 days.

(21) Appl. No.: 13/847,799

(22) Filed: Mar. 20, 2013

(65) Prior Publication Data

US 2013/0297236 A1   Nov. 7, 2013

Related U.S. Application Data

(63) Continuation of application No. 12/213,063, filed on Jun. 13, 2008, now abandoned.

(30) Foreign Application Priority Data

Jun. 21, 2007  (FR) .................................... 07 04446

(51) Int. Cl.
  G01N 27/416   (2006.01)
  G01R 31/12   (2006.01)

(52) U.S. Cl.
  CPC ........ G01R 31/1227 (2013.01); G01N 27/4163 (2013.01)

(58) Field of Classification Search
  CPC ................................................ G01N 27/4163
  See application file for complete search history.

(56) References Cited

U.S. PATENT DOCUMENTS

| | | | |
|---|---|---|---|
| 5,650,061 A | 7/1997 | Kuhr et al. | |
| 5,776,791 A | 7/1998 | Caillat et al. | |
| 6,282,440 B1* | 8/2001 | Brodnick | A61B 5/04011 600/512 |
| 6,428,684 B1 | 8/2002 | Warburton | |

(Continued)

FOREIGN PATENT DOCUMENTS

| | | |
|---|---|---|
| EP | 0-774-662 A1 | 5/1997 |
| JP | A-2006-235669 | 9/2007 |

OTHER PUBLICATIONS

Chibane A., Grangeat P., Desbat L., Voda A.: "Application de modeles a derivee non entiere a la detection electrochimique sur biopuce" Gretsi, 2005, XP002474686.

(Continued)

*Primary Examiner* — Toan Le
*Assistant Examiner* — Manuel Rivera Vargas
(74) *Attorney, Agent, or Firm* — Oliff PLC

(57) ABSTRACT

The method for detecting defective electrodes in an electrode matrix comprises measurement of an electrochemical impedance spectrum for each of the electrodes. Modeling of the spectrum impedance relative to each electrode by means of an implicit non-integral frequency model is performed in the form of a parameter matrix. Principal components analysis of the matrix is performed to transform said parameter matrix into a final matrix containing decorrelated variables representing the parameter matrix in a new space. The distance between each electrode and a reference point is calculated. These calculated distances are compared with a preset threshold distance and the electrodes having a distance greater than the threshold distance are classified as being defective.

10 Claims, 3 Drawing Sheets

(56) References Cited

U.S. PATENT DOCUMENTS

| | | |
|---|---|---|
| 7,043,372 B2 | 5/2006 | Koehler et al. |
| 7,208,077 B1 | 4/2007 | Albers et al. |
| 2002/0157946 A1 | 10/2002 | Winquist et al. |
| 2002/0165675 A1 | 11/2002 | Golovlev |
| 2004/0073390 A1* | 4/2004 | Wagner ............ G01N 33/48728 702/76 |
| 2006/0181262 A1 | 8/2006 | Glenn et al. |

OTHER PUBLICATIONS

"A new electrochemical sensor for heavy-metal ions by the surface-polarization controlling method" Solid-State Sensors, Actuators and Microsystems, 2005. Digest of Technical Papers. Transducers '05. The 13$^{th}$ International Conference on Seoul, Korea. Jun. 5-9, 2005, Piscataway, NJ, USA, IEEE, Jun. 5, 2005, pp. 1876-1879.

Sep. 20, 2012 Office Action issued in U.S. Appl. No. 12/213,063.

* cited by examiner

METHOD FOR DETECTING DEFECTIVE ELECTRODES IN A MICRO-ELECTRODE MATRIX

This application is a continuation of U.S. patent application Ser. No. 12/213,063 filed Jun. 13, 2008. The entire disclosure of which is hereby incorporated by reference in its entirety.

BACKGROUND OF THE INVENTION

The invention relates to a method for detecting defective electrodes in a micro-electrode matrix comprising an impedance measurement of each electrode.

STATE OF THE ART

At present, the fabrication process of the electrodes of a micro-electrode matrix does not enable perfectly well-controlled electrodes to be obtained, either as far as their geometry or their surface is concerned. Moreover, with repeated use, the electrodes are impaired, in particular with formation of a surface oxide and passivation. Likewise, organic residues may form which are difficult to remove by cleaning. This results in an increasingly difficult contact between the electrode and the associated electrolyte. These impairments influence the results obtained with the electrodes. This therefore means that during their lifetime, the electrodes present a behavior which changes for the worse. In order to test whether an electrode is viable, in particular for performing neuronal stimulation, two methods are currently used.

The first method consists in measuring the modula, in Ohms, of the impedance of the electrode at 1 KHz when the latter is placed in the presence of a sodium chloride solution (NaCl) with a concentration of 0.1 mole per liter, which enables the behavior of the electrode at typical stimulation frequencies to be approximately known. The typical frequency is information provided by the manufacturer, and may be very different from that used for neuronal stimulation. With this method, a single measurement enables an idea of this impedance to be given.

The second method used is measurement of the thermal noise. This consists in measuring the peak to peak amplitude measured voltage on the electrode with "no load".

These methods are however fairly simplistic and do not enable a good grasp to be had of the fine behavior of the electrode when it is impaired.

OBJECT OF THE INVENTION

The object of the invention is to remedy these shortcomings, and in particular to provide a method for acquisition of more reliable data and for classifying this data whereby certain electrodes whose behavior is too far removed from the standard behavior can be more finely excluded.

This object is achieved by the fact that the method successively comprises:
measuring an electrochemical impedance spectrum for each of the electrodes,
modeling of the impedance spectrum relative to each electrode by means of an implicit non-integral frequency model, in the form of a parameter matrix,
performing principal components analysis of the matrix, which transforms said parameter matrix into a final matrix containing decorrelated variables representing the parameter matrix in a new space,
calculating the distance between each electrode and a reference point,
comparing the calculated distances with a preset threshold distance, and classifying the electrodes having a distance that is greater than the threshold distance as being defective.

BRIEF DESCRIPTION OF THE DRAWINGS

Other advantages and features will become more clearly apparent from the following description of particular embodiments of the invention given as non-restrictive examples only and represented in the accompanying drawings, in which.

DESCRIPTION OF A PREFERRED EMBODIMENT OF THE INVENTION

Figure 1:
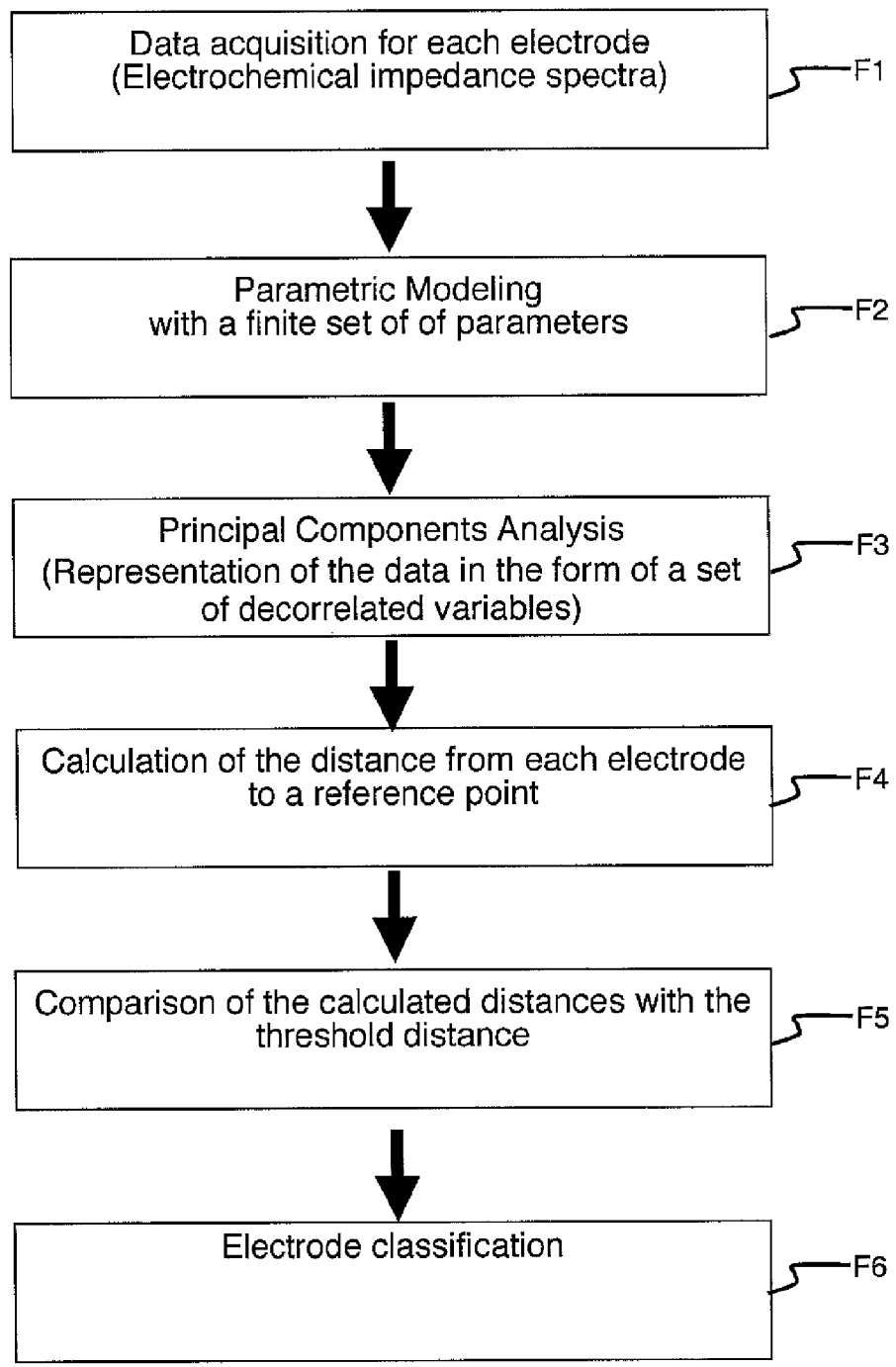
FIG. 1 represents an embodiment of the method according to the invention in schematic form.

As illustrated in FIG. 1, the invention consists in a sequence of steps able to be broken down in the following manner:
Acquisition (F1) of data relative to each electrode by acquisition of electrochemical impedance spectra,
Representation of this data by means of parametric modeling with a finite set of parameters (F2),
Performing principal components analysis of the set of parameters to represent the data obtained in a new set of decorrelated variables (F3),
Calculating the distance d between each electrode and a reference point (F4),
Comparison (F5) of the calculated distance with a threshold distance and classification (F6) of the electrodes to determine the defective electrodes.

Figure 2:
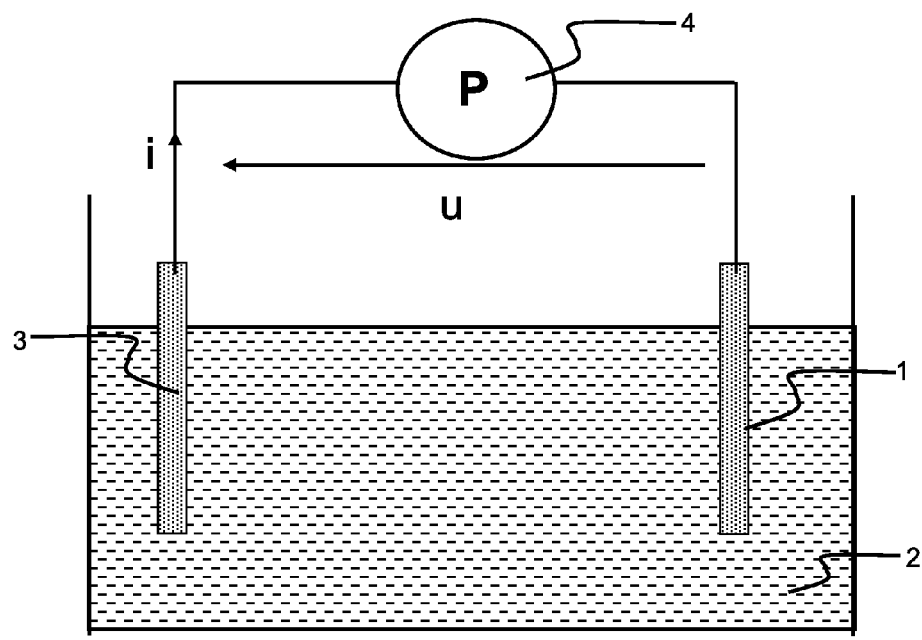
FIG. 2 represents an electrical diagram used for acquisition of data from the electrodes.

FIG. 2 illustrates an electrical diagram able to be used for acquisition of an electrochemical impedance spectrum for each of the electrodes of the matrix.

An electrode 1 to be characterized is immersed in an electrolyte 2, for example a solution containing a known oxidation-reducing couple, preferably hexamine ruthenium chloride (III) $Ru(NH_3)_6Cl_3$. A counter-electrode 3, also immersed in electrolyte 2, is used as reference. Counter-electrode 3 is preferably of Ag/AgCl type.

Electrode 1 to be characterized and counter-electrode 3 are connected to measuring equipment 4, for example a potentiostat, which applies a sine-wave voltage u(t) of low amplitude and of pure frequency around the standard oxidation-reduction potential Eo of the oxidation-reducing couple, used. The sine-wave voltage applied is of the form $u(t)=E_0+V_0 \cos(\omega t)$, in which Vo is a preset amplitude.

Measuring equipment 4 at the same time acquires the intensity i(t) of the current flowing in electrode 1 to be characterized. This intensity i(t) is assimilated to a pure sine-wave of form $i(t)=I \cos(\omega t+\phi)$.

An impedance associated with each electrode can then be deduced from the sine-wave voltage u(t) and the intensity i(t) which is also sine-wave. These operations are repeated for each frequency of the impedance spectrum and for each electrode of the matrix. The sampling frequencies used to achieve the impedance spectrum are conventionally in the 100 Hz-10 kHz range. Furthermore, to achieve an impedance spectrum, at least 10 frequencies are preferably used, and advantageously 20 frequencies are chosen.

For an electrode $1j$ of the electrode matrix, an impedance spectrum of the complete electrochemical cell is thereby obtained for a plurality of frequencies. Parametric identification of an implicit non-integral frequency model for said impedance spectrum is performed. This parametric model is advantageously obtained with the method described in the article by Chibane et al. ("Application de modèles à dérivée non entière à la détection électrochimique sur biopuce", proceedings of the GRETSI 2005 colloquium, 06-09/09/2005 Louvain La Neuve, Belgium). This model takes account of the frequency behavior of the associated electrode and is represented for example in the form:

$$Z(\omega) = Z_0 \frac{1}{(i\omega)^{n_0}} \prod_{p=1}^{N} \left(1 + \frac{i\omega}{\omega_p}\right)^{n_p}$$

where $n_p$ and $\omega_p$ represent the order of the monomial and its cut-off frequency.

This parametric model of the impedance spectrum of electrode 1 to be characterized is represented by a vector A of n dimensions, with n=2N+2, which represents the frequency behavior of the electrochemical cell comprising electrode 1 to be characterized. For example, the vector can be set out in the form $$A = \begin{pmatrix} Z_0 \\ n_0 \\ \omega_1 \\ n_1 \\ \ldots \\ \omega_p \\ n_p \end{pmatrix},$$

This vector A is schematically noted, for the electrode $1j$:

$$A = \begin{pmatrix} x_1(e_j) \\ x_2(e_j) \\ \ldots \\ x_n(e_j) \end{pmatrix},$$

where $x_q(e_j)$ represents the q-th parameter identified for electrode $1j$, with q=1 to n.

Once acquisition of the impedance spectra has been completed for all the electrodes, each electrochemical cell is then represented by a vector A of n dimensions of the type mentioned above. This set of vectors is then grouped in a matrix B which represents the set of k electrodes. Matrix B is represented in the form:

$$B = \begin{pmatrix} x_1(e_1) & x_2(e_1) & \ldots & \ldots & x_n(e_1) \\ x_1(e_2) & x_2(e_2) & \ldots & \ldots & x_n(e_2) \\ \ldots & \ldots & \ldots & \ldots & \ldots \\ x_1(e_k) & x_2(e_k) & \ldots & \ldots & x_n(e_k) \end{pmatrix}$$

where each line represents the parameters associated with an electrode $1j$ and each column represents the parameters $x_q(e_j)$ for the set of electrodes, with q=1 to n, corresponding to the same frequency measurement.

Principal components analysis is used to reduce the number of parameters and thereby extract the maximum amount of information. This analysis comprises standardization and reduction of each parameter $x_q(e_j)$ with respect to the set of parameters $x_q$.

The new variable $x'_q(e_j)$ thus obtained is characterized by the relation:

$$x'_q(e_j) = \frac{(x_q(e_j) - \hat{x}_q)}{\sigma(x_q)}$$

where $\hat{x}_q$ and $\sigma(x_q)$ respectively represent the mean and the standard deviation of the parameters $x_q$ on the set of k electrodes composing the electrode matrix. These two operations enable matrix B to be transformed into a matrix X represented in the form $$X = \begin{pmatrix} x'_1(e_1) & x'_2(e_1) & \ldots & \ldots & x'_n(e_1) \\ x'_1(e_2) & x'_2(e_2) & \ldots & \ldots & x'_n(e_2) \\ \ldots & \ldots & \ldots & \ldots & \ldots \\ x'_1(e_k) & x'_2(e_k) & \ldots & \ldots & x'_n(e_k) \end{pmatrix}$$

A covariance matrix M is then obtained from matrix X by the relation:

$$M = \frac{1}{n-1} X^T X$$

where $X^T$ is the transpose of matrix X. Matrix M is a symmetrical square matrix. The dimension of matrix M is (n×n) if n<k and (k×k) in the opposite case.

Matrix M is diagonalized and the eigenvalues obtained are sorted in decreasing order to form a matrix D. The largest eigenvalues obtained correspond to the principal inertia axes in a new representation space. A matrix V is then obtained from matrices M and D by the relation: $V^T D V = M$.

A matrix Y is then obtained by the formula: Y=XV. Matrix Y thus constitutes a representation of the variables of matrix X, for each electrode to be characterized, in a new representation space where the new variables are then decorrelated. Matrix Y is represented by a set of variables $y_q(e_j)$ corresponding to the q-th parameter of the j-th electrode.

From this matrix Y, it is possible to calculate the distance d between electrode $1j$ and a reference point and to compare it with a previously defined threshold distance. The Mahalanobis distance $d_M$ is preferably used. Representation in graphic form of the set of electrodes at a reference point can be used to make the comparison. Advantageously, the reference point can be the representation of the mean over the set of electrodes.

Figure 3:
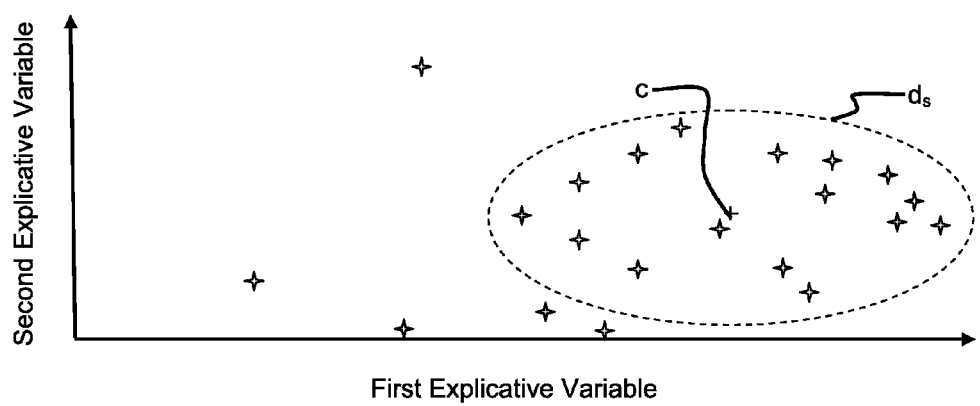
FIG. 3 represents in graphic form the truncated Mahalanobis distance, for two selected variables, of the electrodes with respect to the center of the ellipsoid (reference point) with representation of the threshold distance (with the first variable on the x-axis and the second variable on the y-axis).

In the particular embodiment, FIG. 3 is a representation in graphic form of the truncated Mahalanobis distance from each electrode to the reference point on the two most explicative variables. The threshold distance $d_s$ to reference point c has an ellipsoid shape in the representation chosen and reference point c is characterized by the center of the ellipsoid. Representation in graphic form enables easy and rapid discrimination of the defective electrodes which correspond to the points situated outside the ellipsoid corresponding to threshold distance $d_s$. The value of the threshold can be preset or defined by means of statistical tests.

In an alternative embodiment, a plurality of eigenvalues corresponding to the largest calculated eigenvalues are selected. This enables a plurality of associated variables to be selected for each electrode, reducing the dimensionality of the final matrix and thereby enabling separate analysis of each component for each electrode. In this case, each electrode then has as many components as selected eigenvalues. By reducing the number of eigenvalues, the amount of data to be processed is also reduced. Advantageously, the choice of the number of eigenvalues to be studied is defined according to the margin of error authorized for the result.

In a particular case where the selected eigenvalues and therefore the associated components are for example three in number, the distribution of values of the variables is considered as being gaussian and separable on each component. The reference point used to calculate the distance to the electrode is defined by the gaussian on each component. For each component, the distance from the electrode to the reference point is then preferably translated by calculation of the distance of normality at the associated gaussian. The latter distance is calculated as follows:

$$d = \frac{|y_q(e_j) - m_q|}{\sigma_q}$$

where $m_q$ and $\sigma_q$ represent the mean and the standard deviation of variable $y_q(e_j)$ calculated on all the electrodes.

It is however also possible to obtain a distribution of values considered as being gaussian and separable on each component in the case where more than three variables have been selected.

Figure 4:
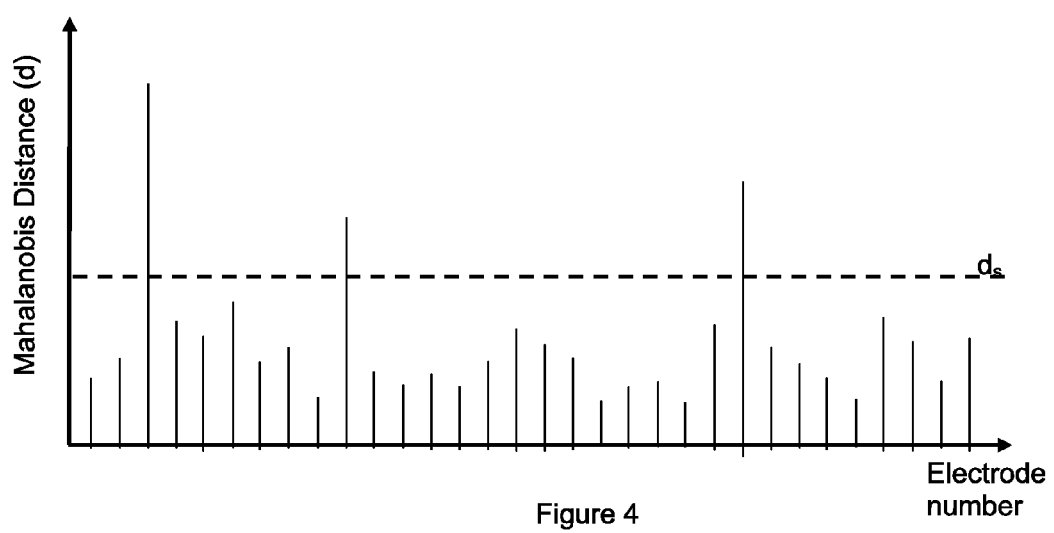
FIG. 4 represents the distance of the electrodes to the mass center of the electrode matrix in graphic form.

For each electrode 1 to be characterized, adding the distances calculated on each of these components enables the distance d to the reference point to be obtained. In this particular case, as illustrated in FIG. 4, representation in graphic form can simply be expressed by the distance d from each electrode to the reference point according to the electrode number (from 1 to n). If the distance d of an electrode is greater than the distance threshold $d_s$, the electrode is then considered to be defective.

The invention claimed is:

1. A method for detecting a defective electrode in an electrode matrix comprising:
    immersing a matrix of electrodes in an electrolyte;
    connecting the matrix of electrodes to a potentiostat that applies a sine-wave signal to the matrix of electrodes;
    measuring an impedance spectrum for one or more electrodes of the electrode matrix when the sine-wave signal is being applied to the matrix of electrodes;
    representing the impedance spectrum by a first set of parameters based on a parametric model;
    calculating a second set of parameters from the first set of parameters;
    calculating a distance between the second set of parameters and a predetermined reference point;
    comparing the calculated distance with a predetermined threshold distance; and
    classifying an electrode of the one or more electrodes as being defective if the calculated distance is greater than the threshold distance.

2. The method according to claim 1, wherein the second set of parameters of the electrode is obtained by reducing a number of variables of the first set of parameters.

3. The method according to claim 1, wherein
    the second set of parameters of the electrode is obtained by performing a principal component analysis to the first set of parameters.

4. The method according to claim 1, wherein the parametric model is an implicit non-integral frequency model.

5. The method according to claim 1, wherein the reference point is calculated from the second set of parameters.

6. The method according to claim 1, wherein the reference point is calculated from the mean over the second set of parameters.

7. The method according to claim 1, wherein the distance is a Mahalanobis distance.

8. The method according to claim 1, wherein the first set of parameters is gathered in a matrix X, each variable of said matrix X, $x'_q(e_j)$ representing the qth parameter of the electrode, the electrode being identified with an integer j, of the 1st set of parameters; and
    the second set of parameters is obtained by performing a principal component analysis to the matrix X, so as to get a matrix Y, each variable of the matrix Y, $y_q(e_j)$, representing the qth parameter of the electrode j of the second set of parameters.

9. The method according to claim 1, wherein
    the measured impedance spectrum is an electrochemical impedance spectrum.

10. The method according to claim 1, wherein
    the method for detecting a defective electrode in an electrode matrix is applied algorithmically to a plurality of electrodes in the electrode matrix.

* * * * *